United States Patent
Pauser (10) Patent No.: US 9,974,629 B2
(45) Date of Patent: May 22, 2018

(54) POWDER JET DEVICE FOR DISPENSING DENTAL MATERIAL

(71) Applicant: 3M INNOVATIVE PROPERTIES COMPANY, St. Paul, MN (US)

(72) Inventor: Helmut Pauser, Diessen (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

(21) Appl. No.: 14/652,384

(22) PCT Filed: Dec. 16, 2013

(86) PCT No.: PCT/US2013/075426
§ 371 (c)(1),
(2) Date: Jun. 15, 2015

(87) PCT Pub. No.: WO2014/099800
PCT Pub. Date: Jun. 26, 2014

(65) Prior Publication Data
US 2015/0327953 A1    Nov. 19, 2015

(30) Foreign Application Priority Data
Dec. 17, 2012 (EP) .................................... 12197572

(51) Int. Cl.
*A61C 3/025* (2006.01)
*A61C 1/00* (2006.01)
*A61C 1/08* (2006.01)

(52) U.S. Cl.
CPC ............ *A61C 3/025* (2013.01); *A61C 1/0084* (2013.01); *A61C 1/087* (2013.01)

(58) Field of Classification Search
CPC ........ A61C 3/025; A61C 1/087; A61C 1/0084
See application file for complete search history.

(56) References Cited

U.S. PATENT DOCUMENTS 2,529,004 A    11/1950   Eley
3,939,599 A     2/1976   Henry
(Continued)

FOREIGN PATENT DOCUMENTS

CA    1225262    8/1987
CH     656524    7/1986
(Continued)

OTHER PUBLICATIONS

Haffajee, "The effect of SRP on the clinical and microbiological parameters of periodontal diseases," Journal of Clinical Periodontology, 1997, vol. 24, No. 5, pp. 324-334.
(Continued)

*Primary Examiner* — Michael D Abreu
(74) *Attorney, Agent, or Firm* — Melissa E. Buss (57) ABSTRACT

A powder jet device (10) for dispensing a dental material comprises a nozzle head (12) comprising a discharge nozzle. The powder jet device (10) further comprises a housing (14) comprising a valve portion (28), which is connected to the nozzle head (12) and is adapted to receive a valve member (16), and a chamber portion (30) comprising at least a first chamber (32) for storing a powder material. The chamber portion (30) comprises a proximal end (34) located adjacent the valve portion (28), a distal end (36) located away from the valve portion (28) and a fluid channel (38) extending from the distal end (36) substantially to the proximal end (34) into the chamber. The powder jet device (10) further comprises a valve member (16) disposed within the valve portion (28). The valve member (16) comprises a fluid supply passage (54) and is movable between a first position, in which a first fluid path (64) for delivery of a fluid from the fluid supply passage (54) into the chamber via the fluid channel (38) so as to create a dispersion from the powder material and a second fluid path (66) for delivery of the
(Continued)

dispersion to the discharge nozzle are open, and a second position, in which at least the first fluid path (64) is closed.

13 Claims, 5 Drawing Sheets

(56) References Cited

U.S. PATENT DOCUMENTS

| | | |
|---|---|---|
| 3,972,123 A | 8/1976 | Black |
| 4,078,558 A | 3/1978 | Woog |
| 4,184,258 A | 1/1980 | Barrington |
| 4,248,589 A | 2/1981 | Lewis |
| 4,266,535 A | 5/1981 | Moret |
| 4,492,575 A * | 1/1985 | Mabille .................. A61C 3/025 251/5 |
| 4,595,365 A | 6/1986 | Edel |
| 4,676,749 A | 6/1987 | Mabille |
| 5,120,219 A | 6/1992 | De Farcy |
| 5,158,455 A | 10/1992 | Bailey |
| 5,306,144 A | 4/1994 | Hibst |
| 5,833,456 A | 11/1998 | Davis |
| 5,857,851 A | 1/1999 | Chavanne |
| 6,054,119 A | 4/2000 | Hurme |
| 6,126,444 A | 10/2000 | Horiguchi |
| 6,238,211 B1 | 5/2001 | Esrock |
| 6,293,856 B1 | 9/2001 | Hertz |
| 6,485,304 B2 | 11/2002 | Beerstecher |
| 6,648,644 B1 | 11/2003 | Flemmig |
| 6,884,070 B2 | 4/2005 | Cevey |
| 7,083,411 B2 | 8/2006 | Flemmig |
| 7,175,430 B1 | 2/2007 | Gasser |
| 7,762,812 B2 | 7/2010 | Pichat |
| 7,980,923 B2 | 7/2011 | Olmo |
| 8,210,846 B2 | 7/2012 | Duineveld |
| 2001/0021496 A1 | 9/2001 | Aumuller |
| 2002/0123020 A1 | 9/2002 | Aumuller |
| 2002/0127513 A1 | 9/2002 | Bachmann |
| 2003/0008263 A1 | 1/2003 | Cook |
| 2003/0129560 A1 | 7/2003 | Atkin |
| 2004/0166474 A1 | 8/2004 | Gugel |
| 2006/0121411 A1 | 6/2006 | Wiek |
| 2009/0317758 A1 | 12/2009 | Duineveld |
| 2010/0029757 A1 | 2/2010 | Hellerbrand |
| 2010/0151413 A1 | 6/2010 | Andersson |
| 2010/0297576 A1 | 11/2010 | Donnet |
| 2011/0117523 A1 | 5/2011 | Cook |
| 2011/0281238 A1 | 11/2011 | Cook |

FOREIGN PATENT DOCUMENTS

| | | |
|---|---|---|
| CN | 2032047 | 2/1989 |
| CN | 2321545 | 6/1999 |
| CN | 2440591 | 8/2001 |
| DE | 3538324 | 5/1986 |
| DE | 4123019 | 1/1993 |
| EP | 0097288 | 1/1984 |
| EP | 0119021 | 9/1984 |
| EP | 0119735 | 9/1984 |
| EP | 0163610 | 12/1985 |
| EP | 0299229 | 1/1989 |
| EP | 1145689 | 10/2001 |
| EP | 1468659 | 10/2004 |
| EP | 2070505 | 6/2009 |
| ES | 8800833 | 2/1988 |
| FR | 2575062 | 6/1986 |
| FR | 2583630 | 12/1986 |
| FR | 2588182 | 4/1987 |
| FR | 2599244 | 12/1987 |
| GB | 1211150 | 11/1970 |
| GB | 1480594 | 7/1977 |
| GB | 2026359 | 2/1980 |
| JP | 58041550 | 3/1983 |
| JP | 11104148 | 4/1999 |
| JP | 2000-051235 | 2/2000 |
| JP | 2000-083966 | 3/2000 |
| JP | 2001-204741 | 7/2001 |
| JP | 2002-153490 | 5/2002 |
| JP | 2002-165806 | 6/2002 |
| JP | 2002-209911 | 7/2002 |
| JP | 2003-116880 | 4/2003 |
| KR | 20100008362 | 8/2010 |
| WO | WO 1989-07932 | 9/1989 |
| WO | WO 1994-00078 | 1/1994 |
| WO | WO 1996-12447 | 5/1996 |
| WO | WO 1997-04741 | 2/1997 |
| WO | WO 1998-08906 | 3/1998 |
| WO | WO 1999-20197 | 4/1999 |
| WO | WO 2000-53154 | 9/2000 |
| WO | WO 2001-36159 | 5/2001 |
| WO | WO 2001-72273 | 10/2001 |
| WO | WO 2002-13721 | 2/2002 |
| WO | WO 2002-74180 | 9/2002 |
| WO | WO 2003-003934 | 1/2003 |
| WO | WO 2003-011164 | 2/2003 |
| WO | WO 2003-043519 | 5/2003 |
| WO | WO 2003-075784 | 9/2003 |
| WO | WO 2004-075770 | 9/2004 |
| WO | WO 2005-007008 | 1/2005 |
| WO | WO 2005-106734 | 11/2005 |
| WO | WO 2005-115645 | 12/2005 |
| WO | WO 2007-034612 | 3/2007 |
| WO | WO 2007-134336 | 11/2007 |
| WO | WO 2009-148907 | 12/2009 |
| WO | WO 2010-010360 | 1/2010 |
| WO | WO 2011-123123 | 10/2011 |
| WO | WO 2013-191903 | 12/2013 |
| WO | WO 2014-099490 | 6/2014 |
| WO | WO 2014-099495 | 6/2014 |

OTHER PUBLICATIONS

Axelsson, "The significance of maintenance care in the treatment of periodontal disease," Journal of Clinical Periodontology, 1981, vol. 8, No. 4, pp. 281-294.
Zappa, "Root Substance Removal by Scaling and Root Planing," Journal of Periodontology, Dec. 1991, vol. 62, No. 12, pp. 750-754.
Flemmig, "Working Parameters of a Magnetostrictive Ultrasonic Seale Influencing Root Substance Removal In Vitro," Journal of Periodontology 1998, vol. 69, pp. 547-553.
Boyde, Airpolishing Effects on Enamel, Dentine, Cement and Bone, British Dental Journal, Apr. 21, 1984, vol. 156, pp. 287-291.
Sauro, "Dentine desensitization induced by prophylactic and air-polishing procedures: An in vitro dentine permeability and confocal microscopy study," Journal of Dentistry 2010, vol. 38, pp. 411-422.
International Search Report for PCT International Application No. PCT/US2013/075426, dated Mar. 4, 2014, 3 pages.

* cited by examiner

POWDER JET DEVICE FOR DISPENSING DENTAL MATERIAL

FIELD OF THE INVENTION

The present invention relates to a device for dispensing a dental material to a desired location, for example the tooth structure of a patient, and more particularly to a powder jet device.

BACKGROUND ART

In dentistry powder jet devices are currently used for applying a fluid stream of abrasive particles, air and water to the tooth structure of a patient, for example for cleaning or pretreating the tooth surfaces.

Generally, a powder jet device may comprise a nozzle head through which the fluid stream can be delivered. Typically the fluid stream contains powder particles which are dispersed and entrained by an air stream guided through a powder containing chamber, and a liquid optionally added to the air/powder mixture, for example through a separate nozzle. In a device of that type used for cleaning tooth surfaces the powder material often comprises dental abrasive particles, and the liquid is normally water.

Examples of powder jet devices for dispensing dental materials are described in U.S. Pat. No. 3,972,123 (Black); U.S. Pat. No. 4,676,749 (Mabille); GB-A-2 026 359 (Gallant); JP-A-11104148 (Micron KK); US-A-2003/0129560 (Atkin et al.); and WO 03/011164 (Medivance Instruments Limited).

Despite the advantages provided by the above-identified devices, there is still a potential for improvements thereof. Particularly, some powder materials, when delivered through a nozzle of a powder jet device, may tend to block the nozzle. That may be the case, especially (but not exclusively), if the powder comes into contact with a liquid (e.g. a stream of water as described above, or even just moisture) as it emerges from the nozzle head because the powder may become damp and flow less freely than when it is dry. In a more extreme case, the powder may be intended to form a hardenable paste or gel when mixed with the fluid and can, therefore, be expected to block the nozzle unless removed. Summarizing, the main reason for the above-mentioned defect is that all media are delivered in parallel or at the same time. After delivery, remaining media get in contact within the nozzle and still cause clogging. Current approaches to solve this problem are to spatially divert the media as far as possible. However, this approach involves severe constructional modifications.

Further there is a general desire to minimize the costs for manufacturing the devices. There is also a desire to use different powder materials with the same type of device. Still further, there is a desire to control the flow rate of the overall fluid stream as well as the mixing ratio between components forming the fluid stream.

According to the above, it is an object of the present invention to provide a powder jet device which helps minimizing the costs for manufacturing, which is easy to use and which helps minimizing the costs in the medical treatment.

SUMMARY OF THE INVENTION

The present invention relates to a powder jet device for dispensing a dental material. The powder jet device comprises a nozzle head which is adapted for receiving a discharge nozzle. The powder jet device further comprises a housing which comprises a valve portion being adapted to receive a valve member. Further the housing comprises a chamber portion comprising at least a first chamber for storing or holding a powder material. The chamber portion comprises a proximal end located adjacent the valve portion, a distal end located farther away from the valve portion, and a fluid channel opening adjacent the distal end (36) into the first chamber.

The powder jet device further comprises a valve member movably disposed within the valve portion. The valve member comprises a fluid supply passage and a first and a second fluid path branching off from the fluid supply passage. The first fluid path is provided for guiding a fluid from the fluid supply passage into the first chamber via the fluid channel so as to create a dispersion from the fluid and the powder material. The second fluid path is provided for delivery of the dispersion toward the discharge nozzle. The valve member is movable between a first position, in which the first fluid path and the second fluid path are open, and a second position, in which at least the first fluid path is closed.

The present invention may be advantageous in that the powder jet device essentially consists only of three parts, for example the nozzle head, the housing and the valve member, such that the manufacturing costs are relatively low. Particularly, these three parts may be at least partially (and preferably entirely) made of plastics such that the manufacturing costs may be minimized. Further, because the fluid channel extends substantially between the distal end and the proximal end into the first chamber, the powder within the first chamber is completely dispersed because the fluid is enabled to pass substantially all of the powder. Particularly, the fluid may pass the powder from the bottom to the top if the powder jet device is held with the chamber portion generally vertical with the distal end of the chamber portion downwards and the proximal end upwards. In this orientation of the chamber portion the powder due to gravity tends to flow toward the distal end of the chamber portion where the fluid may enter the first chamber. Therefore the fluid can pass substantially all of the powder present in the first chamber in a direction against the direction of gravity. Thus the powder may be consistently aerated and kept in flow, and blocking of the powder may be avoided.

The discharge nozzle head preferably comprises a first discharge channel and a second discharge channel each opening at a free end of the nozzle head and being in fluid communication with (an inside of) the valve portion. The nozzle head is further preferably adapted for releasably, and preferably rotatably, attaching the discharge nozzle to the free end of the nozzle head. The discharge nozzle preferably forms a common discharge channel into which the first and second discharge channel merge, when the discharge nozzle is placed on the nozzle head.

In the device the first discharge channel is preferably provided for guiding the dispersion toward the free end of the nozzle head. Further the second discharge channel may be provided for guiding only the fluid or the fluid with a further powder and/or a liquid dispersed in the fluid, toward the free end of the nozzle head. The second discharge channel preferably coaxially surrounds the first discharge channel at least adjacent the free end of the nozzle head. The fluid preferably is a gas, in particular air.

The valve member and the valve portion preferably are adapted to form, in combination, a valve for controlling within the device an internal flow of a fluid supplied from an external source into the powder jet device. In particular the valve is preferably adapted for entirely blocking the internal flow, for enabling the flow or a reduced flow, for splitting the fluid supply in partial internal flows, and for adjusting or blocking any flow or partial flows. The fluid channel may extend substantially between the distal end and the proximal end within the first chamber, and preferably may extend over only a partial length of the first chamber.

The valve portion may extend generally along a first longitudinal axis and the chamber portion may extend at an angle in a range from 70 degrees to 140 degrees with respect to the first longitudinal axis. Such a design may provide a relatively ergonomic design without substantially increasing the manufacturing costs. The fluid channel may extend generally parallel within the chamber portion (at an angle in a range from 70 degrees to 140 degrees with respect to the first longitudinal axis).

The fluid supply passage of the valve member may extend along a second longitudinal axis, which may be co-aligned with the first longitudinal axis. The first fluid path is a channel, which is in fluid communication with the fluid supply passage and extends at least partially in a radial direction from the fluid supply passage with respect to the second longitudinal axis of the fluid supply passage. Further the second fluid path is a channel comprising a first portion, which is in fluid communication with the fluid supply passage and extends parallel to the second longitudinal axis of the fluid supply passage, and a second portion, which is in fluid communication with the first portion and extends at least partially in a radial direction from the fluid supply passage with respect to the second longitudinal axis of the fluid supply passage. The first portion and the second portion of the second fluid path preferably merge with each other at an angle which provides for a Venturi effect upon a fluid flowing through the first portion. More particularly, this design is adapted to guide a part of the fluid flow into the first chamber via the first fluid path for creating the dispersion from the powder material, and to suck (through the second portion of the second fluid path due to the venture effect) the dispersion out off the first chamber by another part of the fluid flow guided through the first portion of the second fluid path. The first portion of the second fluid path may have a conical shape with the cone widening toward the first portion of the second fluid path. Thus any powder sucked from the first chamber may be hindered from accumulating within the first portion of the second fluid path. Accordingly, the dispersion may be reliably supplied towards the discharge nozzle without creating any dead zones of the fluid flow within the first chamber or blocking within the device. Additionally accumulation of any residual powder within the first chamber may further be prevented.

An extension at least partially is to be understood in the sense of the present invention in that the concerning constructional member does not have to exclusively extend in a radial direction but in that the extension may also comprise a component of the extension in an axial direction. Thus, the expression “at least partially in a radial direction” encompasses also deviations from an exact radial direction. Accordingly, the constructional member may extend in a radial direction as well as an axial direction and a combination thereof.

One or more of the first fluid path and the second portion of the second fluid path may be inclined toward an axial direction with respect to the second longitudinal axis of the fluid supply passage. Such a design may be helpful in controlling, for example maximizing, the Venturi effect. Thus, even if the fluid flows with a relatively low velocity, a creation of a dispersion of the powder and the liquid and a reliable supply thereof toward the discharge nozzle may be achieved.

An inclination toward an axial direction is to be understood in the sense of the present invention in that the respective constructional member does not extend exactly radially but extends in a direction between the axial and radial direction.

The valve member may comprise a nozzle head side end facing the nozzle head and a connector side end adapted to be connected to a fluid supply line. One or both of the first fluid path and the second portion of the second fluid path are preferably inclined towards the second longitudinal axis of the fluid supply passage if seen from the connector side end to the nozzle head side end. This design serves to further enhance the venturi effect. Thus, even if the fluid flows with a lower velocity, a creation of a dispersion from the powder and a reliable supply thereof to the discharge nozzle may be ensured.

The chamber portion may comprise a second chamber for storing a liquid. Further the valve member is preferably further movable between a third position, in which a third fluid path for delivery of a fluid into the second chamber and a fourth fluid path for delivery of the liquid from the second chamber to the discharge nozzle are open, and a fourth position, in which at least the third fluid path is closed. Accordingly the valve member is preferably selectively movable to the first, second, third or fourth position, for example as desired by a user. In one or both of the third position and the fourth position of the valve member, at least the first fluid path may be closed. This design allows for supplying at least two different media without changing the device or the supply line. Thus, the operation time may be minimized because a change of the device or the supply is not necessary.

The valve member is preferably movable between any of the first, second, third and fourth position and thus is adapted to enable a continuous adjustment of a mixing ratio between the fluid, the powder and the liquid. Preferably the valve member is steplessly movable, meaning without retention at certain predetermined positions, although a stepwise motion (including a retention at certain predetermined positions) may be likewise provided for the valve member.

Preferably the third fluid path is a channel, which is in fluid communication with the fluid supply passage and extends at least partially in a radial direction from the fluid supply passage with respect to the second longitudinal axis of the fluid supply passage. Further preferably the fourth fluid path is a channel comprising a third portion, which is in fluid communication with the fluid supply passage and extends parallel to the second longitudinal axis of the fluid supply passage, and a fourth portion, which is in fluid communication with the third portion and extends at least partially in a radial direction from the fluid supply passage with respect to the second longitudinal axis of the fluid supply passage. This design improves the supply of the liquid as the fluid may force the liquid out off the second chamber.

Preferably the first fluid path is circumferentially offset about the second longitudinal axis relative to the third fluid path. Thus, using the first chamber or the second chamber may be appropriately selected by an operator by rotating the valve member around the second longitudinal axis into the desired position.

The first chamber and the second chamber are preferably disposed adjacent to each other and arranged side by side with respect to a direction parallel to the second longitudinal axis. This design is compact and allows forming the chamber portion in the form of a magazine such that an operator is not obstructed during operating.

The valve member may form a rotary valve with the valve portion of the housing. Thus, the respective chamber may be easily selected by rotating the valve member. Thus, the individual chambers may be sealed and may be refilled by means of the rotary valve.

The nozzle head may comprise a rotatable knob adapted to rotate the valve member. This design allows an operator to rotate the valve member with a single hand without a change of the handgrip. Thus, the operation time may be further minimized because a change of the device is not necessary and its operation position may be easily changed.

The valve member may be made of plastics. This allows manufacturing the valve member by means of injection molding. Further, if the valve member is made of plastics, the sealing properties of the valve member for preventing a leakage of the powder may be maximized.

The valve member may comprise at least one passage for filling the first chamber. The valve member is preferably movable relative to the valve portion between an opening position, in which the passage is open and the first chamber communicates with an exterior of the housing, and a closing position, in which the passage is closed and the first chamber is blocked from communicating with the exterior of the housing. This design allows easy refilling of the chamber.

The chamber portion may comprise a third chamber for storing a further powder material. Thus, different powders for different applications may be discharged with a single device. Further, the valve allows changing between cleaning, air polishing and disinfection as it allows selecting different chambers, or combinations of different chambers with each other for operation of the powder jet device.

In one embodiment of the present invention the powder jet device has a housing with one or more chambers. For example, a chamber for a cleaning powder, a chamber for a polishing powder and a chamber for a disinfection liquid may be provided. Any chamber or combination of one or more chambers with each other for operation of the powder jet device may be selected centrally by the rotary valve. The rotary valve can preferably be actuated by use the rotary nozzle head. For example, the nozzle head may comprise a rotary knob, which is adapted to rotate the valve member if actuated by an operator. Further, as the fluid channel extends from the proximal end to substantially the distal end, the powder within the first chamber is reliably dispersed as the fluid passes the powder from the distal end towards the proximal end after entering the first chamber. This effect is combined with a venturi effect created by another part of the fluid flowing within the second fluid path. Accordingly, there are two flows of the fluid. The first flow enters the first chamber through the fluid channel and creates the dispersion. The second flow flows through the second fluid path and sucks the dispersion out of the first chamber based on the venturi effect.

BRIEF DESCRIPTION OF THE FIGURES

By way of example, a powder jet device in accordance with the invention will now be described with reference to the accompanying drawings, in which.

DETAILED DESCRIPTION OF THE INVENTION

The device 10 shown in the drawings is a powder jet device of a type for use in the dental field for applying a powder/gas mixture and a liquid to the tooth structure of a patient.

Figure 1:
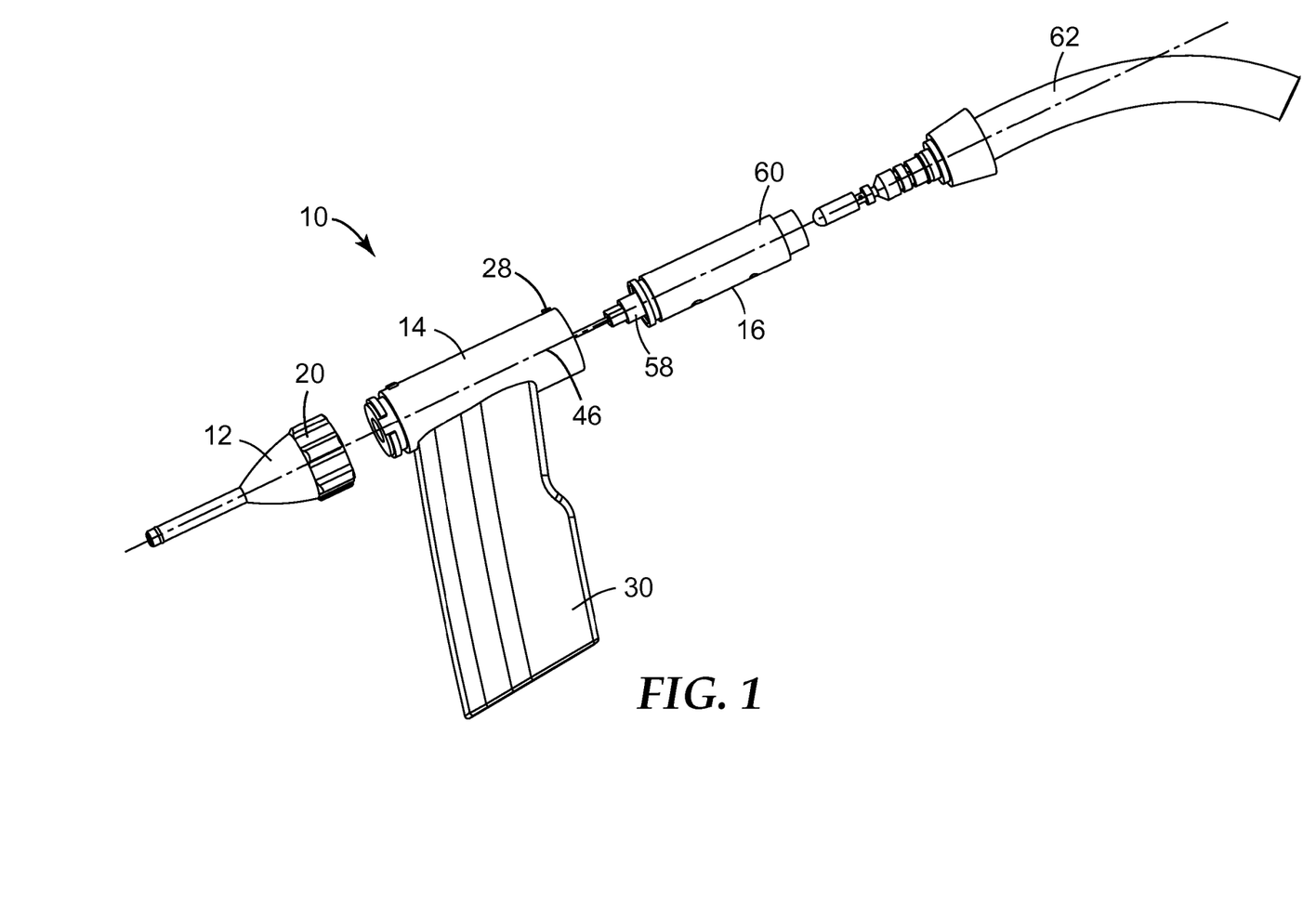
FIG. 1 is an explosion view of the powder jet device.
Figure 2:
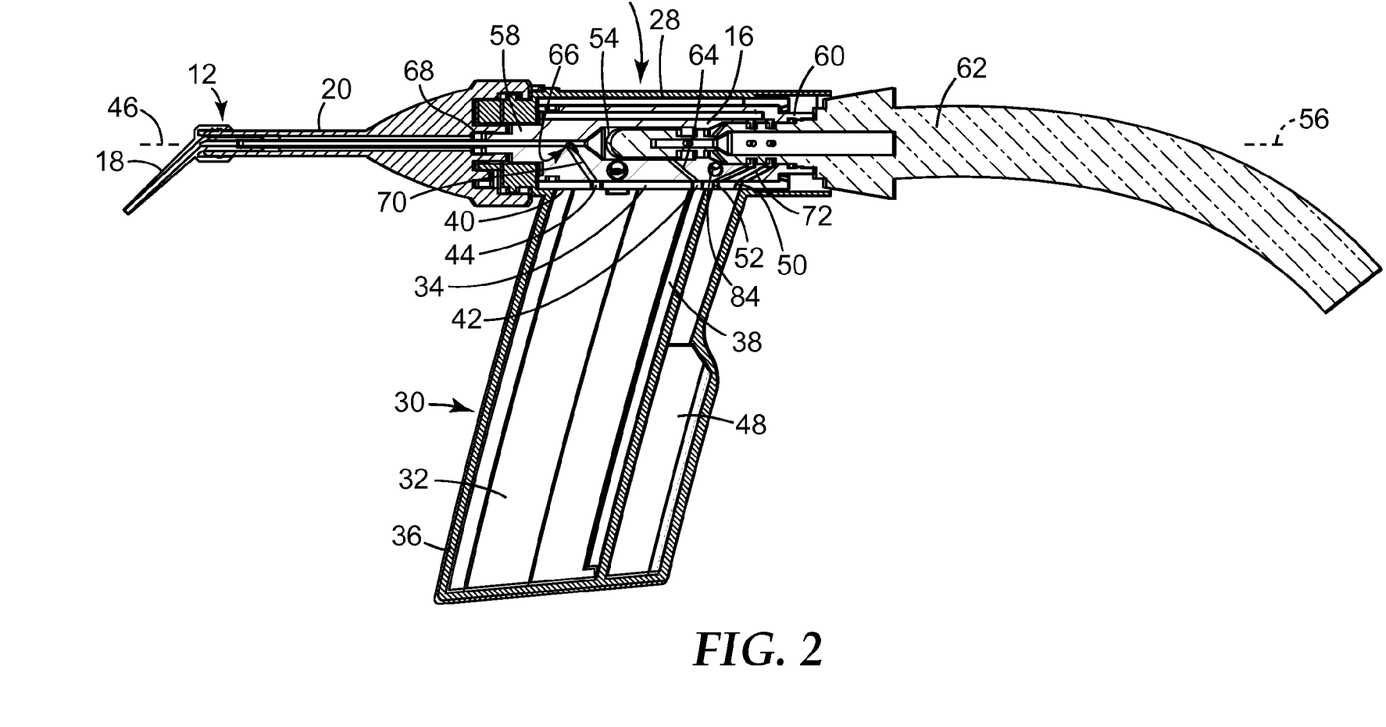
FIG. 2 shows a longitudinal cross-section of the powder jet device.

FIG. 1 shows an explosion view of a powder jet device 10 for dispensing a dental material according to the present invention. The powder jet device comprises a nozzle head 12, a housing 14 and a valve member 16. The nozzle head 12 comprises a discharge nozzle 18 (FIG. 2). The nozzle head 12 further comprises a rotatable knob 20. The rotatable knob 20 is adapted to rotate the valve member 16 as will be explained in more detail below. The nozzle head 12 may be designed such that an operator holding the nozzle head 12 or the housing 14 may rotate the knob 20.

Figure 5:
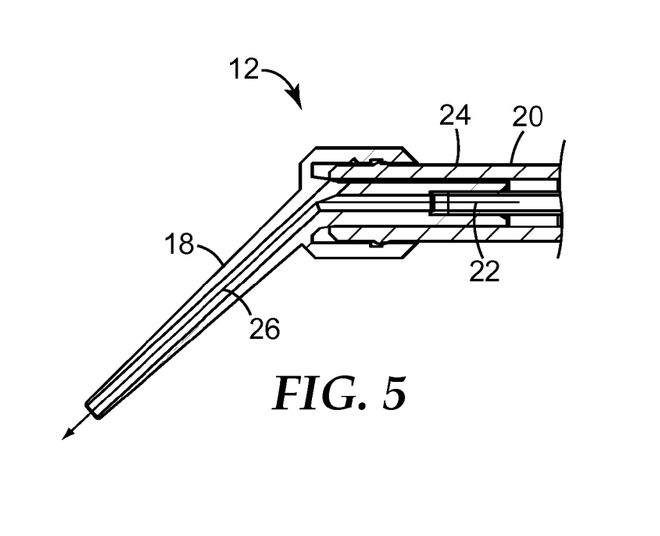
FIG. 5 is a longitudinal cross-section of the nozzle head showing the delivery of different media.

FIG. 5 shows a longitudinal cross-section of the nozzle head 12. The nozzle head 12 comprises a first discharge channel 22 and a second discharge channel 24, which are disposed parallel, in particular preferably coaxial, to one another. The first discharge channel 22 and the second discharge channel 24 open into a common discharge channel 26 disposed within the discharge nozzle 18. Due to the preferably coaxial arrangement of the first discharge channel 22 and the second discharge channel 24 the nozzle head is freely rotatable on the knob 20 without affecting the fluid communication between the common discharge channel 20 and the first and second discharge channel 22, 24. Further the ends of the first discharge channel 22 and the second discharge channel 24 are arranged relative to each other such that a Venturi effect is formed (for example the second discharge channel 24 may be arranged such that—when a fluid flows through the second discharge channel 24—a suction at the end of the first discharge channel is created, or vice versa).

FIG. 2 shows a longitudinal cross-section of the device 10. The housing 14 comprises a valve portion 28. The valve portion 28 is removably connected to the nozzle head 12. The valve portion 28 is adapted to receive the valve member 16 as will be explained in more detail below. The housing 14 further comprises a chamber portion 30. The chamber portion 30 comprises at least a first chamber 32 for storing a powder material. The powder material may comprise abrasive particles which are used in dentistry. For example, the abrasive particles may be used to remove plaque, soft calculus, stains and discolorations from the teeth of dental patients as will be further explained below. The chamber portion 30 may be designed substantially in the form of a magazine. The chamber portion 30 comprises a proximal end 34 located adjacent the valve portion 28. The chamber portion 30 further comprises a distal end 36 located away from the valve portion 28. Still further, the chamber portion 30 comprises a fluid channel 38 extending from the proximal end 34 substantially to the distal end 36 and which opens into the first chamber 32. This means, the fluid channel 38 opens adjacent the bottom of the housing 14.

The valve portion 28 and the chamber portion 30 are separated from one another by means of a wall portion 40 of the housing 14, which is located between the valve portion 28 and the chamber portion 30 at the proximal end 34. The wall portion 40 comprises a first orifice 42 through which the valve portion 28 can fluidly communicate with the fluid channel 38. The wall portion 40 further comprises a second orifice 44 through which the valve portion 28 can fluidly communicate with the first chamber 32.

The valve portion 28 extends along a first longitudinal axis 46. The chamber portion 30 extends at an angle in a range from 70 degrees to 140 degrees with respect to the first longitudinal axis 46. The particular range for the angle is to be understood in that the angle is seen in a direction of the longitudinal axis 46 from the housing 14 towards the nozzle head 12, wherein an acute angle is defined in that the chamber portion 30 of the housing is inclined away from the nozzle head 12 which is an inclination to the right or in the counter-clockwise direction with respect to the illustration in FIG. 2 and an obtuse angle is defined in that the chamber portion 30 of the housing 14 is inclined towards the nozzle head 12 which is an inclination to the left or in the clockwise direction with respect to the illustration in FIG. 2. For example, in the exemplary embodiment shown in FIG. 2, the chamber portion extends at an angle of 120 degrees with respect to the first longitudinal axis 46. The fluid channel 38 extends at an angle of 120 degrees with respect to the first longitudinal axis 46. The extension of the fluid channel 38 may be defined by means of a central axis of the fluid channel. Thus, the fluid channel 38 extends parallel to side walls of the chamber portion 30.

The chamber portion 30 further comprises a second chamber 48 for storing a liquid. The liquid may be water or a concentrated liquid which will be mixed with water in an adjustable ratio. The chamber portion 30 may further comprise further chambers (not shown) for storing other or further media. For example, the chamber portion 30 may comprise a third chamber (not shown) for storing a further powder material. The first chamber 32 and the second chamber 48 are disposed adjacent to each other in a direction of the first longitudinal axis 46. The first chamber 32 is arranged closer to the nozzle head 12 than the second chamber 48 if seen in the direction of the first longitudinal axis 46 from the housing 14 towards the nozzle head 12. The wall portion 40 comprises a third orifice 50 and a fourth orifice 52 through which the valve portion 28 can fluidly communicate with the second chamber 48. The wall portion 40 may comprise further orifices (not shown) in case the chamber portion 30 comprises further chambers through which the valve portion 28 is in fluid communication with the chambers.

The valve member 16 is disposed within the valve portion 28. The valve member 16 with the valve portion 28 of the housing 14 preferably forms a rotary valve. The valve member 16 is made of plastics. It is preferred that the valve member 16 is made of soft plastics in order to ensure sealing between the valve member 16 and the housing 14. For example, the valve member 16 may be made of plastics like for example PP, HDPE, POM, PBT, or any other suitable plastic material particularly, hard plastics are abraded by the powder material from the first chamber 32 as the abrasive particles attack the plastics. Soft plastics resist to a more extent such attacks. The valve member 16 comprises a fluid supply passage 54. The fluid supply passage 54 of the valve member 16 extends along a second longitudinal axis 56. The second longitudinal axis 56 defines a central axis of the valve member 16. In a state, in which the valve member 16 is disposed within the valve portion 28, the first longitudinal axis 40 of the valve portion 28 and the second longitudinal axis 56 of the fluid supply passage 54 of the valve member 16 fall together. Particularly, the valve member 16 comprises a nozzle head side end 58 facing the nozzle head 12 and a connector side end 60 adapted to be connected to a fluid supply line 62. The fluid supply passage 54 extends along the second longitudinal axis 56 from the connector side end 60 to the nozzle head side end 58. The fluid supply passage 54 extends coaxially with respect to the second longitudinal axis 56. The valve member 16 is substantially cylindrical, wherein the diameter of the nozzle head side end 58 is smaller than the diameter of the connector side end 60. For example, the valve member 16 may be formed stepped conical at the nozzle head side end 58.

The valve member 16 further comprises a first fluid path 64 for delivery of a fluid from the fluid supply passage 54 into the first chamber 32 via the fluid channel 38. This means that the first fluid path 64 branches off from the fluid supply passage 54. The first fluid path 64 is a channel which is in fluid communication with the first chamber 32 by means of the fluid channel 38. The first fluid path 64 extends at least partially in a radial direction from the fluid supply passage 54. For example, the first fluid path 64 extends at an angle of 70 degrees with respect to the second longitudinal axis 56. Accordingly, the first fluid path 64 is inclined to the right or in the counter-clockwise direction with respect to the illustration in FIG. 2. The valve member 16 further comprises a second fluid path 66 which is in fluid communication with the fluid supply passage 64 via the first chamber 32. Particularly, the second fluid path 66 is disposed closer to the nozzle head 12 than the first fluid path 64 if seen in the direction of the second longitudinal axis 56 from the connector side end 60 towards the nozzle head side end 58. Similarly, the second fluid path 66 is a channel comprising a first portion 68, which is in fluid communication with the fluid supply passage 54 and extends parallel to the second longitudinal axis 56 of the fluid supply passage 54, and a second portion 70, which is in fluid communication with the first portion 68 and extends at least partially in a radial direction from the fluid supply passage 54 with respect to the second longitudinal axis 56 of the fluid supply passage 54. Particularly, the second portion 70 of the second fluid path 56 extends at an angle of 70 degrees with respect to the second longitudinal axis 56. Accordingly, the second portion 70 of the second fluid path 56 is inclined to the right or in the counter-clockwise direction with respect to the illustration in FIG. 2. Thus, one or more of the first fluid path 64 and the second portion 70 of the second fluid path 66 are inclined in an axial direction with respect to the second longitudinal axis 56 as they only partially extend in a radial direction. Further, the first fluid path 64 and the second portion 70 of the second fluid path 66 are parallel to one another if seen in the direction of the longitudinal direction and if seen in a circumferential direction around the second longitudinal axis 56 of the fluid supply passage 54. It is to be noted that the fluid supply passage 54 may be designed in dependence of the connector of the fluid supply line 52. For example, the fluid supply passage 54 may be formed as a hole which conically tapers towards the nozzle head side end 58.

The valve member 16 further comprises a third fluid path 72 for delivery of a fluid into the second chamber 48 and a fourth fluid path 74 for delivery of the liquid from the second chamber 48 to the discharge nozzle 18. For example, the third fluid path 72 and the fourth fluid path 74 fluidly communicate with a connector of the fluid supply line 62 by means of ring channels 75. The third fluid path 72 is a channel which is in fluid communication with the fluid supply passage 54 and extends at least partially in a radial direction from the fluid supply passage 54 with respect to the second longitudinal axis 56 of the fluid supply passage 54. The fourth fluid path 74 is a channel comprising a third portion 76, which is in fluid communication with the fluid supply passage 54 and extends parallel to the longitudinal axis 56 of the fluid supply passage 54, and a fourth portion 78, which is in fluid communication with the third portion 76 and extends at least partially in a radial direction from the fluid supply passage 54 with respect to the second longitudinal axis 56 of the fluid supply passage 54. The fourth portion 78 of the fourth fluid path 74 and the third fluid path 72 extend at an angle of 120 degrees with respect to the second longitudinal axis 56. Accordingly, the fourth portion 78 of the fourth fluid path 74 and the third fluid path 72 are inclined to the left or in the clockwise direction with respect to the illustration in FIG. 2. The fourth portion 78 of the fourth fluid path 74 and the third fluid path 72 are parallel to one another if seen in the direction of the longitudinal direction and if seen in a circumferential direction around the second longitudinal axis 56 of the fluid supply passage 54. The fourth portion 78 of the fourth fluid path 74 is arranged closer to the nozzle head 12 than the third fluid path 72. The fourth portion 78 of the fourth fluid path 74 and the third fluid path 72 are shifted in a circumferential direction around the second longitudinal axis 56 relative to the first fluid path 64 and the second portion 70 of the second fluid path 66. For example, the fourth portion 78 of the fourth fluid path 74 and the third fluid path 72 are shifted 20 degrees in a circumferential direction around the second longitudinal axis 56 relative to the first fluid path 64 and the second portion 70 of the second fluid path 66. The third portion 76 of the fourth fluid path 74 opens into an annular space 80 located at the nozzle head side end 58 of the valve member 16. The annular space 80 is formed such that the third portion 76 of the fourth fluid path 74 is in fluid communication with the second discharge channel 24 in the rotatable knob 20 by means of the annular space 80.

The valve member 16 further comprises a first passage 82 for filling the first chamber 32 and a second passage 84 for filling the second chamber 48. The first passage 82 and the second passage 84 are arranged perpendicular with respect to the second longitudinal axis 56 and are offset from the fluid supply passage 54. Thus, the first passage 82 and the second passage 84 do not intersect the fluid supply passage 54. The first passage 82 and the second passage 84 are through holes penetrating the valve member 16 in a direction perpendicular with respect to the second longitudinal axis 56. This means, the first passage 82 and the second passage 84 are arranged radially outwards with respect to the second longitudinal axis 56.

Figure 3:
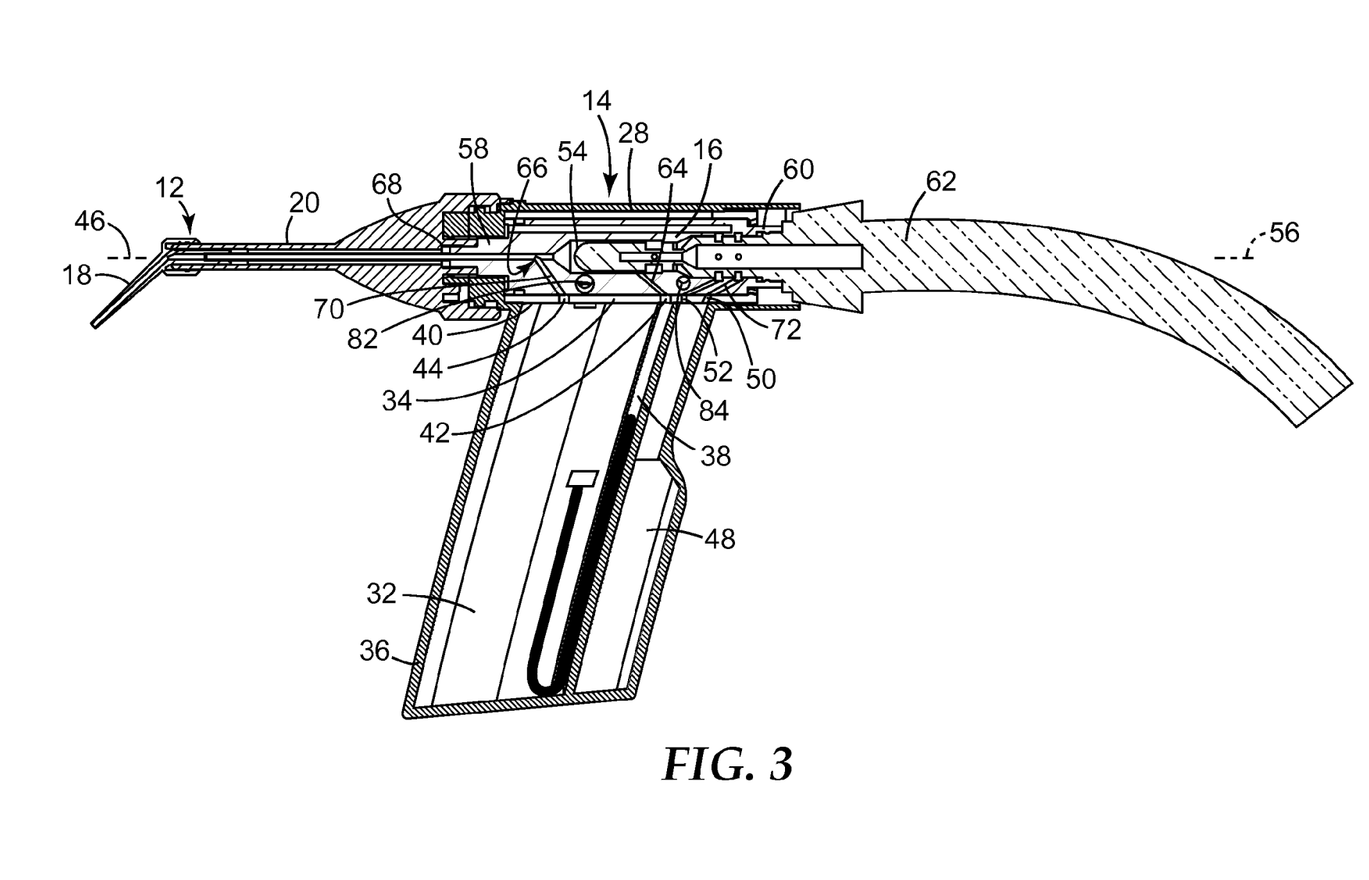
FIG. 3 is a further longitudinal cross-section of the powder jet device showing a first function principle of the device.

The operation of the powder jet device 10 will now be explained. FIG. 3 shows a first functional principle of the powder jet device 10 for discharging a powder dispersion. The valve member 16 is movable at least between a first position and a second position. In the first position, the first fluid path 64 for delivery of a fluid from the fluid supply passage 54 into the first chamber 32 via the fluid channel 38 and the second fluid path 56 are open. The fluid may be air. Particularly, the valve member 16 is rotated by means of the rotatable knob 20 such that the first fluid path 64 overlaps with the first orifice 42. Thus, a first part of the fluid may flow from the fluid supply passage 54 through the first fluid path 64 and the first orifice 42 into the first fluid channel 38. The fluid then flows from the proximal end 34 to the distal end 36 within the first fluid channel 38. The fluid then flows out off the first fluid channel 38 at the distal end 36 and enters the first chamber 32. As the flowing fluid passes the powder within the first chamber 32, it creates a dispersion from the powder material for delivery of the dispersion to the discharge nozzle 18. A second part of the fluid flows within the second fluid path 66. More particularly, the second part of the fluid flows within the first portion 68 which is in fluid communication with the fluid supply passage 54. As the fluid is usually supplied with a high velocity with powder jet devices 10, the fluid flowing within the first portion 68 causes a venturi effect and sucks the created dispersion out off the first chamber through the second portion 70 of the second fluid path 66 by means of the generated negative pressure. The second part of the fluid and the created dispersion then mix with one another within the first portion 68. The dispersion mixed with the second part of the fluid then flows to the first discharge channel 22 and then to the common discharge channel 26 as shown in FIG. 5. Subsequently, the dispersion mixed with the second part of the fluid then flows out off the nozzle head 12 through the discharge nozzle 18. In the first position, the fluid may not enter the second chamber 48 as the third fluid path 72 and the fourth portion 78 of the fourth fluid path 74 are shifted relative to the first fluid path 64 and the second portion 70 of the second fluid path 66 in the circumferential direction.

The valve member 16 may be rotated into the second position by means of the rotatable knob 20. In the second position, at least the first fluid path 64 is closed. As the first fluid path 64 and the second portion 70 of the second fluid path 66 are parallel to one another, also the second portion 70 of the second fluid path 66 is closed. More particularly, in the second position, the first fluid path 64 does not overlap with the first orifice 42. Thus, the first fluid path 64 is shifted away from the fluid channel 38 such that the fluid from the fluid supply passage 54 may not enter the fluid channel 38 and the first chamber 32 via the first fluid path 64. Accordingly, the first fluid path 64 does not fluidly communicate with the fluid channel 38 and the first chamber 32 in the second position of the valve member 16.

Figure 4:
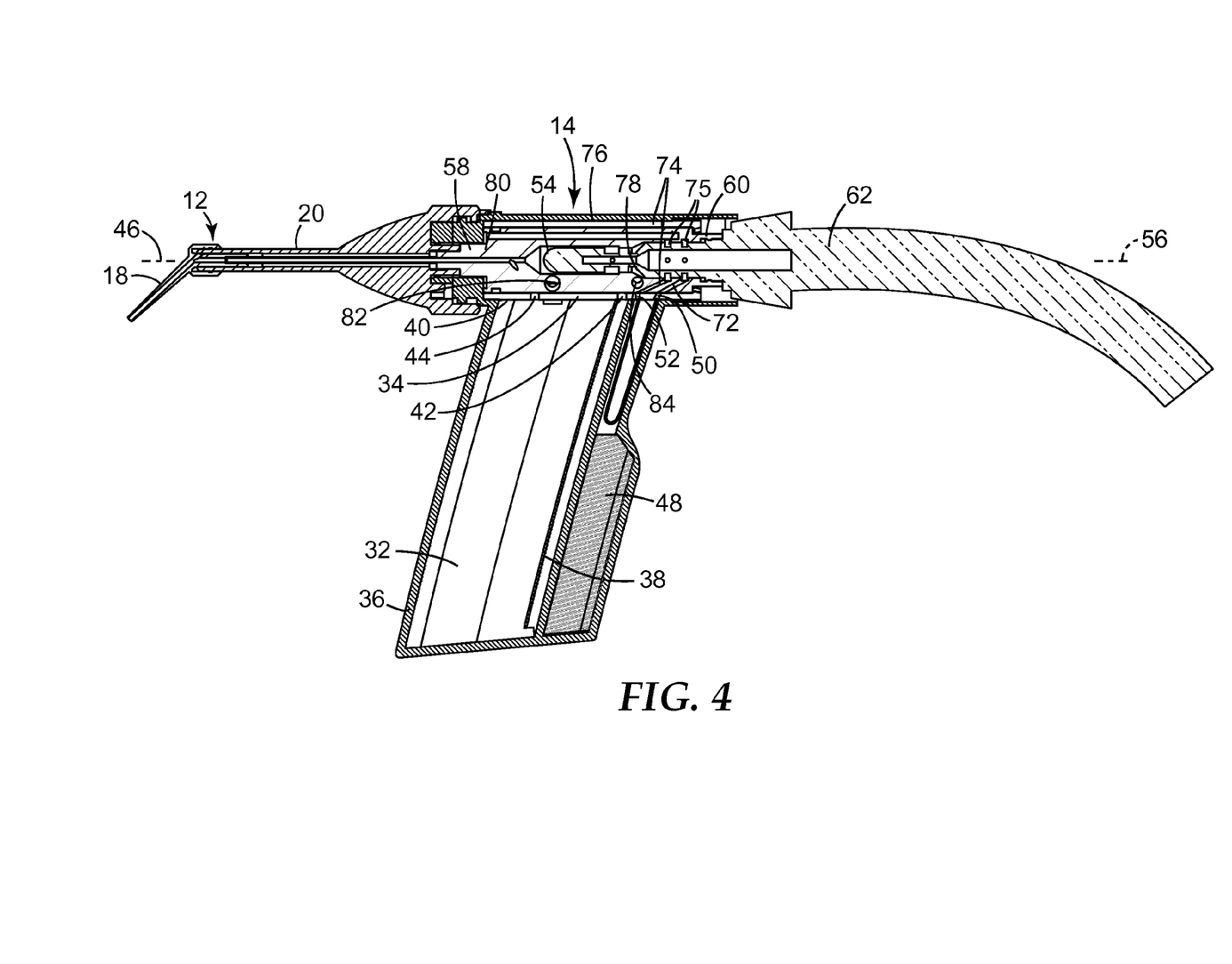
FIG. 4 is a further longitudinal cross-section of the powder jet device showing a second function principle of the device.

FIG. 4 shows a first functional principle of the powder jet device 10 for discharging a liquid. The valve member 16 is further rotatable between a third position and a fourth position. In the third position, the third fluid path 72 for delivery of the fluid into the second chamber 48 and the fourth fluid path 74 for delivery of the liquid from the second chamber 48 to the discharge nozzle 18 are open. More particularly, in the third position, the third fluid path 72 overlaps with the third orifice 50. Thus, a first part of the fluid may flow from the fluid supply passage 54 through the third fluid path 72 and the third orifice 50 into the second chamber 48. The fluid having entered the second chamber 48 generates an excess pressure which forces the liquid out off the second chamber 48 through the fourth portion 78 of the fourth fluid path 74 and into the third portion 76 of the fourth fluid path 74. The liquid forced out off the second chamber may be mixed with the fluid. The liquid is then supplied into the annular space 80, flows then through the second discharge channel 24 and through the common discharge channel 26. Subsequently, the liquid flows out off the nozzle head 12 through the discharge nozzle 18. It is to be noted that the second position and the third position may be identical or different positions depending on the respective application of the powder jet device 10.

The valve member 16 may be rotated into the fourth position by means of the rotatable knob 20. In the fourth position, at least the third fluid path 72 is closed. As the third fluid path 72 and the fourth portion 78 of the fourth fluid path 74 are parallel to one another, also the fourth portion 78 of the fourth fluid path 74 is closed. More particularly, in the fourth position, the third fluid path 72 does not overlap with the third orifice 50. Thus, the third fluid path 72 is shifted away from the second chamber 48 such that the fluid from the fluid supply passage 54 may not enter the second chamber 48. Accordingly, the third fluid path 72 does not fluidly communicate with the second chamber 48 in the fourth position of the valve member 16. Further, in one or more of the third position and the fourth position of the valve member 16, at least the first fluid path 64 is closed as they are shifted in a circumferential direction relative to one another.

Figure 6:
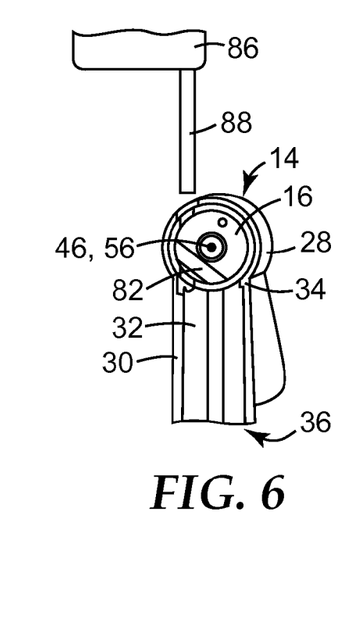
FIG. 6 is a cross-section of the housing of the powder jet device showing a step of filling a chamber.

FIG. 6 shows a cross-section view of the powder jet device 10 at the housing 14. The valve member 16 may further be rotated between a first opening position and a first closing position. FIG. 6 shows the valve member 16 in the first closing position. In the closing position, the first passage 82 is closed and the first chamber 32 is blocked from communicating with an exterior of the housing 14.

Figure 7:
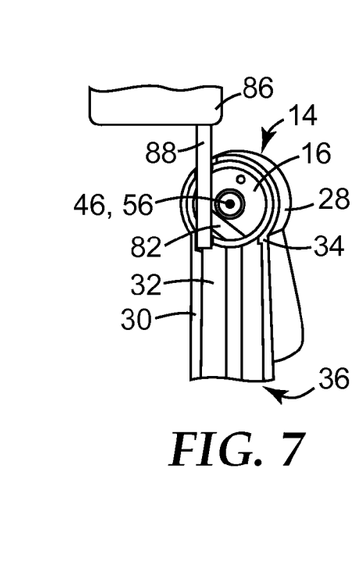
FIG. 7 is a cross-section of the housing of the housing of the powder jet device showing another step of filling the chamber.

FIG. 7 shows another cross-section view of the powder jet device 10 at the housing 14. Particularly, FIG. 7 shows the valve member 16 in the first opening position. In the first opening position, the first passage 82 is open and the first chamber 32 communicates with an exterior of the housing 14. Thus, first chamber 32 may be filled by means of a filling device 86. For example, the filling device 86 may comprise a tube 88 which is inserted into the first passage 82 in order to fill the first chamber 32.

Similarly, the valve member 16 may be rotated between a second opening position, in which the second passage 84 is open and the second chamber 48 communicates with an exterior of the housing 14, and a second closing position, in which the second passage 84 is closed and the second chamber 48 is blocked form communicating with the exterior of the housing 14. The liquid may be filled into the second chamber 48 by means of a similar filling device in the second opening position.

It is explicitly noted that the fluid paths mention herein may be arranged such that a discharge of the created powder dispersion and the liquid at the same time is possible. For example, further or other fluid paths may be arranged at the valve member parallel to one another in the circumferential direction so as to allow the fluid to enter the first chamber 32 and the second chamber 48 at the same time. Needless to say, the created dispersion and the liquid may be supplied out off the first chamber 32 and the second chamber 48 at the same time if the fluid paths are correspondingly arranged parallel to one another. Depending on the size and the position of the orifices and the rotation positions of the valve member, an adjustable mixing ratio of the dispersion and the liquid is possible. For example, the valve member may be rotated in further positions in which the orifices are exposed to different degrees so as to change the amount of fluid flowing therethrough. For example, the valve member may be rotated into positions in which the first orifice 42 is blocked at an amount of 25%, 50%, 75% or the like of its opening area. Thus, the amount of fluid flowing through the first fluid path 64 into the first chamber 32 is correspondingly changed. This also changes the amount of the dispersion flowing out off the first chamber 32 through the second portion 70 of the second fluid path 66. Accordingly, the valve member 16 allows a flow rate control of the dispersion. At the same time, the valve member 16 is adapted to deblock the second orifice 44 at an amount of 75%, 50%, 25% or the like of its opening area. Thus, the amount of fluid flowing into the second chamber 48 is changed in that the amount decreases if the amount of fluid flowing into the first chamber increases and vice versa. This means for this example that the ratio of the mixture from liquid and powder dispersion changes from 25% powder dispersion and 75% liquid to a ratio of 50% powder dispersion and 50% liquid and to 75% powder dispersion and 25% liquid. Of course, the supply of one of the mentioned media may be totally blocked or deblocked in the above steps or other steps as explained above. Particularly, the opening areas of the orifices may be independently blocked and deblocked so as to allow a flow rate control of the medias from chambers. Therefore, the powder jet device 10 of the present invention allows to deliver powder and liquid in a controlled manner simultaneously or independently. The rotatable knob may be designed to be rotatable in a stepwise manner, wherein the steps correspond to different positions of the valve member. For example, the rotatable knob may comprise a latching mechanism allowing the valve member to releasably latch or fix in the first position, the second position, the third position, the fourth position and the like. Thus, an unwanted change of the operation position is reliably prevented and the valve member may rest in the respective position.

The invention claimed is:

1. A powder jet device for dispensing a dental material, comprising:
   a nozzle head for receiving a discharge nozzle, wherein the nozzle head comprises a rotatable knob adapted to rotate a valve member,
   a housing comprising:
   a valve portion removably connected to the nozzle head and adapted to receive the valve member, wherein the valve portion extends along a first longitudinal axis, and
   a chamber portion comprising a magazine that extends at an angle with respect to the first longitudinal axis of the valve portion, the chamber portion comprising at least a first chamber for storing a powder material, wherein the chamber portion comprises a proximal end located adjacent the valve portion, a distal end located farther away from the valve portion, and a fluid channel extending generally parallel within the chamber portion and opening adjacent the distal end into the first chamber, and
   a valve member movably disposed within the valve portion, wherein the valve member forms a rotary valve with the valve portion of the housing and comprises a fluid supply passage and a first and a second fluid path branching off from the fluid supply passage, wherein the valve member is movable between a first position, in which the first fluid path for delivery of a fluid from the fluid supply passage into the first chamber via the fluid channel so as to create a dispersion from the fluid and the powder material and the second fluid path for delivery of the dispersion toward the discharge nozzle are open, and a second position, in which at least the first fluid path is closed.

2. The device of claim 1, wherein the fluid supply passage of the valve member extends along a second longitudinal axis, wherein the first fluid path is a channel, which is in fluid communication with the fluid supply passage and extends at least partially in a radial direction from the fluid supply passage with respect to the second longitudinal axis of the fluid supply passage, and the second fluid path is a channel comprising a first portion, which is in fluid communication with the fluid supply passage and extends parallel to the second longitudinal axis of the fluid supply passage, and a second portion, which is in fluid communication with the first portion and extends at least partially in a radial direction from the fluid supply passage with respect to the second longitudinal axis of the fluid supply passage.

3. The device of claim 2, wherein the chamber portion comprises a second chamber for storing a liquid, wherein the valve member is further movable between a third position, in which a third fluid path for delivery of a fluid into the second chamber and a fourth fluid path for delivery of the liquid from the second chamber to the discharge nozzle are open, and a fourth position, in which at least the third fluid path is closed, and wherein in one or both of the third position and the fourth position of the valve member, at least the first fluid path is closed.

4. The device of claim 3, wherein the valve member is steplessly movable between any of the first, second, third and fourth position and thus is adapted to enable a continuous adjustment of a mixing ratio between the fluid, the powder and the liquid.

5. The device of claim 3, wherein the third fluid path is a channel, which is in fluid communication with the fluid supply passage and extends at least partially in a radial direction from the fluid supply passage with respect to the second longitudinal axis of the fluid supply passage, and the fourth fluid path is a channel comprising a third portion, which is in fluid communication with the fluid supply passage and extends parallel to the second longitudinal axis of the fluid supply passage, and a fourth portion, which is in fluid communication with the third portion and extends at least partially in a radial direction from the fluid supply passage with respect to the second longitudinal axis of the fluid supply passage.

6. The device of claim 3, wherein the first fluid path is circumferentially offset in a direction around the second longitudinal axis relative to the third fluid path.

7. The device of claim 3, wherein the first chamber and the second chamber are disposed side by side.

8. The device according to claim 2, wherein one or both of the first fluid path and the second portion of the second fluid path are inclined toward an axial direction with respect to the second longitudinal axis of the fluid supply passage.

9. The device of claim 2, wherein the valve member comprises a nozzle head side end facing the nozzle head and a connector side end adapted to be connected to a fluid supply line, wherein one or both of the first fluid path and the second portion of the second fluid path are inclined towards the second longitudinal axis of the fluid supply passage if seen from the connector side end to the nozzle head side end.

10. The device of claim 1, comprising a first discharge channel for guiding the dispersion toward a free end of the nozzle head, and a second discharge channel for guiding a further fluid toward the free end of the nozzle head, and wherein the second discharge channel coaxially surrounds the first discharge channel at least adjacent the free end.

11. The device of claim 1, wherein the valve member is made of plastics.

12. The device of claim 1, wherein the valve member comprises at least one passage for filling the first chamber, wherein the valve member is movable between an opening position, in which the passage is open and the first chamber communicates with an exterior of the housing, and a closing position, in which the passage is closed and the first chamber blocked from communicating with the exterior of the housing.

13. The device of claim 1, wherein the chamber portion comprises a third chamber for storing a further powder material.

* * * * *

UNITED STATES PATENT AND TRADEMARK OFFICE
CERTIFICATE OF CORRECTION

PATENT NO. : 9,974,629 B2
APPLICATION NO. : 14/652384
DATED : May 22, 2018
INVENTOR(S) : Helmut Pauser Page 1 of 1

It is certified that error appears in the above-identified patent and that said Letters Patent is hereby corrected as shown below:

On the Title Page

Item (54) and in the Specification, Column 1, Line 1, after "DISPENSING" insert -- A --.

Signed and Sealed this
Ninth Day of April, 2019

Andrei Iancu
*Director of the United States Patent and Trademark Office*